United States Patent
Yamamoto

(10) Patent No.: US 9,851,330 B2
(45) Date of Patent: Dec. 26, 2017

(54) RAPID, HIGHLY-SENSITIVE, AND HIGHLY-SPECIFIC NUCLEIC ACID DETECTION

(71) Applicant: KONICA MINOLTA LABORATORY U.S.A., INC., San Mateo, CA (US)

(72) Inventor: Noriaki Yamamoto, Tokyo (JP)

(73) Assignee: KONICA MINOLTA LABORATORY U.S.A., INC., San Mateo, CA (US)

( * ) Notice: Subject to any disclaimer, the term of this patent is extended or adjusted under 35 U.S.C. 154(b) by 0 days.

(21) Appl. No.: 15/063,355

(22) Filed: Mar. 7, 2016

(65) Prior Publication Data

US 2016/0299100 A1    Oct. 13, 2016

Related U.S. Application Data

(60) Provisional application No. 62/136,044, filed on Mar. 20, 2015.

(51) Int. Cl.
G01N 27/447        (2006.01)
C12Q 1/68          (2006.01)

(52) U.S. Cl.
CPC ..... *G01N 27/44791* (2013.01); *C12Q 1/6827* (2013.01); *G01N 27/447* (2013.01); *G01N 27/44721* (2013.01)

(58) Field of Classification Search
CPC ........ G01N 27/447; G01N 27/00; C12Q 1/68; C07H 21/04
See application file for complete search history.

(56) References Cited

U.S. PATENT DOCUMENTS 5,445,933 A * 8/1995 Eadie ................ C12Q 1/6823
                                                      435/6.15
5,482,832 A * 1/1996 Lens ................. C12Q 1/6816
                                                      435/5

(Continued)

OTHER PUBLICATIONS

Zhang et al., "Optimizing the specificity of nucleic acid hybridization", Nature Chemistry (2012), vol. 4, pp. 208-214, Mar. 2012 (published online Jan. 22, 2012.

(Continued)

*Primary Examiner* — Narayan Bhat
(74) *Attorney, Agent, or Firm* — Chen Yoshimura LLP

(57) ABSTRACT

A nucleic acid (NA) detection method combines ultra-specific probe, on-chip isotachophoresis (ITP) which can separate single strand and double strand NAs, and enzyme amplification. The ITP device has a sieving matrix between the LE (leading electrolyte) and TE (trailing electrolyte) reservoirs, for separating double-strand and single-strand NAs. The LE or TE reservoir also contains a spacer ion having a mobility between the LE and the TE. The sample and a double-strand NA probe is added to the TE reservoir, the probe being formed of a protector strand modified with a fluorescent molecule and a complement strand, where the protector strand is released in the presence of the target NA. Fluorescent signal is detected downstream of the sieving matrix. Alternatively, the protector strand is modified with an enzyme and a single-strand NA modified with a substrate of the enzyme is added to the reaction mixture downstream of the sieving matrix.

3 Claims, 6 Drawing Sheets

(56) References Cited

U.S. PATENT DOCUMENTS

| 8,658,361 B2* | 2/2014 | Wu ..................... | C12Q 1/6818 |
| | | | 422/430 |
| 2010/0081138 A1* | 4/2010 | Frechon ................ | C07H 21/00 |
| | | | 435/6.15 |

OTHER PUBLICATIONS

Eid et al., "Isotachophoresis with ionic spacer and two-stage separation for high sensitivity DNA hybridization assay", Analyst (2013), 138, pp. 3117-3120.

* cited by examiner

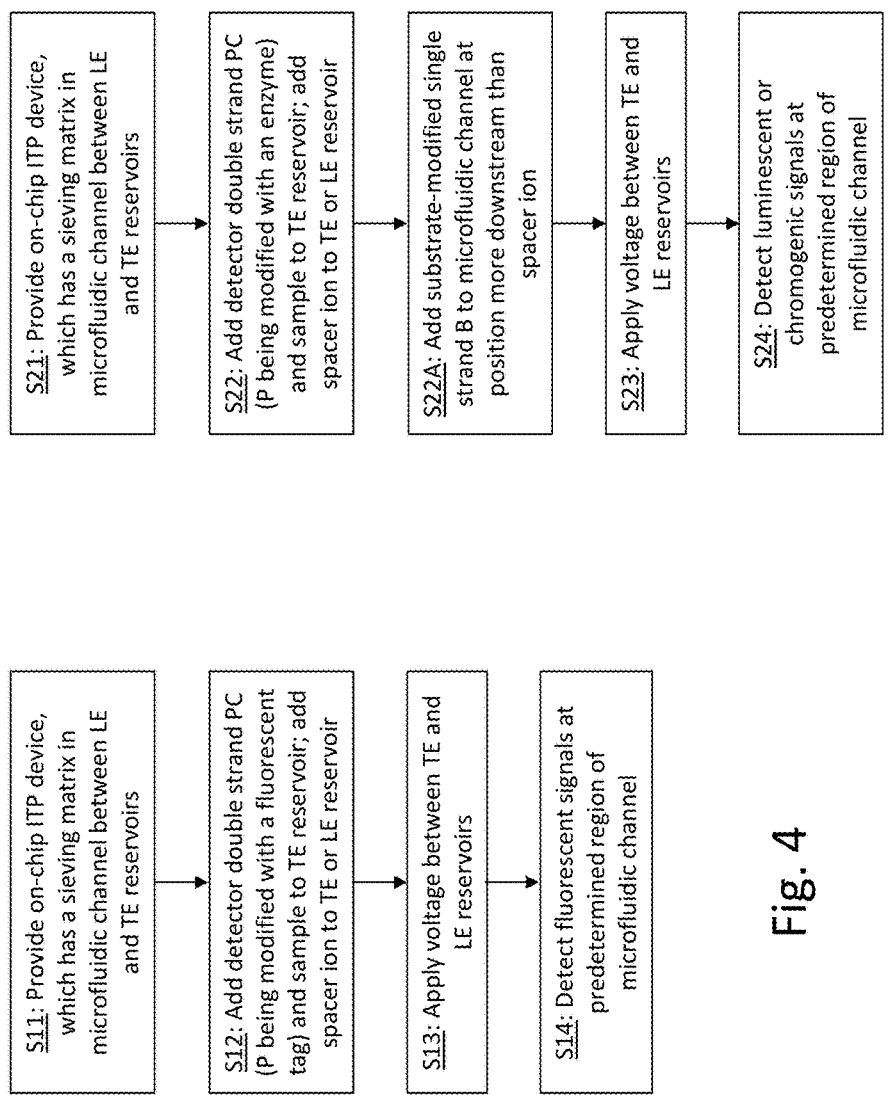

RAPID, HIGHLY-SENSITIVE, AND HIGHLY-SPECIFIC NUCLEIC ACID DETECTION

BACKGROUND OF THE INVENTION

Field of the Invention

This invention relates to nucleic acid (NA) detection, and in particular, it relates to a method that employs ultra-specific probe, isotachophoresis (ITP), and enzyme amplification to achieve rapid, highly-sensitive, and highly-specific NA detection.

Description of Related Art

An ultra-specific probe which can discriminate single nucleotide mutations with high-specificity is described in Optimizing the specificity of nucleic acid hybridization, D. Y. Zhang, S. X. Chen, P. Yin, Nature Chemistry (2012), Vol. 4, 208-214, March 2012 (published online Jan. 22, 2012) ("Zhang et al. 2012"). As shown in FIG. 1 (adapted from FIG. 2 of the above article; in FIG. 1, shading patterns schematically represent the sequences where the same shading pattern represent the same sequence, and the dots between two sequences indicate that the two sequences are complementary to each other), the ultra-specific probe used in this technology (called "toehold exchange probe") is a double strand-DNA (PC) consisting of a protector strand (P) and a complement strand (C). The complement strand C has a longer sequence than the protector strand P. A part of the complement strand C is 100% complementary with the target sequence X. Because the affinity between the target sequence X and the complement strand C is higher than that between the protector strand P and the complement strand C, in the presence of target X, the protector strand P is displaced and a target-C double strand is formed. However, if the DNA to be tested has more than one mutation relative to the target sequence (i.e. it is a non-target, denoted "spurious target S" in FIG. 1), the affinity between the non-target S and the complement strand C is lower than that between the protector strand P and the complement strand C, and the strand displacement (or exchange) reaction does not occur. By detecting the target-C double strand or the isolated protector strand P, the amount of the target sequence X can be measured with high-specificity.

Isotachophoresis (ITP) is an electrophoresis technique that uses two buffers including a high mobility leading electrolyte (LE) and a low-mobility trailing electrolyte (TE). In peak-mode ITP, sample species bracketed by the LE and TE focus into a narrow TE-to-LE interface. Due to the high concentration of sample species in a small volume at the interface, high efficiency (rapid) molecular-molecular interaction can occur.

On-chip isotachophoresis (ITP) is a technology that can realize ultra-rapid reactions by focusing the sample in the solution. Isotachophoresis with ionic spacer and two-stage separation for high sensitivity DNA hybridization assay, Charbel Eid, Giancarlo Garcia-Schwarz and Juan G. Santiago, Analyst (2013), 138, 3117-3120 ("Eid et al. 2013"), describes a technique of ultra-rapid DNA hybridization and subsequent single strand- and double strand-DNA separation using ITP. As illustrated in FIG. 2, adopted from FIG. 1 of Eid et al. 2013, ITP is used to enhance NA hybridization and an ionic spacer molecule is used to subsequently separate the reaction product. In the first stage, the probe and target are focused and mix rapidly in free solution under ITP. The reaction mixture then enters a region of the microfluidic channel containing a sieving matrix, which allows the spacer ion to overtake the slower double strand NA and separate it from the single strand NA.

Eid et al. 2013 describes its FIG. 1 as follows (p. 3118, left column): "Our assay includes a spacer ion with intermediate mobility which forms a plateau region between the LE and TE, thereby creating two sharp interfaces between the LE and spacer and between the spacer and TE. FIG. 1a demonstrates the steps in our reaction-separation assay. First, we leverage ITP to focus the probe and target molecules and accelerate second-order hybridization kinetics (time 1). The second and third stages of the assay, denoted respectively by t2 and t3, employ a linear sieving matrix to separate the reaction products. The channel initially contains two LE regions in series, as shown in FIG. 1b. LE1 includes no sieving matrix, while LE2 includes a sieving matrix. The sieving matrix primarily affects mobility of DNA molecules relative to small ions. In the LE1 region, spacer ions have an electrophoretic mobility lower than that of the probe, target, and probe-target complexes. This enables simultaneous rapid mixing and preconcentration of the probe and its target. Upon entering LE2, the spacer ions overtake the now slower target and probe-target complex. The spacer has sufficient initial concentration to quickly form a plateau ITP region which separates excess probes from probes hybridized to target molecules. In this final stage, the excess probe molecules continue to focus between the LE and the spacer, while the probe-target complexes focus in a separate ITP zone between the spacer and the TE. This enables sensitive detection of the probe-target complexes in the absence of unhybridized fluorescent probe molecules."

SUMMARY

While the toehold exchange probe technology described in Zhang et al. 2012 achieves high specificity, there is a need to increase its sensitivity and speed. On the other hand, while ultra-specific probe used in ITP can achieve rapid and high-specific reaction, the sensitivity is still an issue.

The present invention is directed to a method and related apparatus for NA detection that substantially obviates one or more of the problems due to limitations and disadvantages of the related art.

An object of the present invention is to improve sensitivity of the ultra-specific probe in ITP.

By using enzyme reaction and the capability of ITP to separate single strand-NA and double strand NA, the NA detection methods according to embodiments of the present invention can realize high-sensitivity detection with high-specificity and rapid speed.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and/or other objects, as embodied and broadly described, the present invention provides a method for detecting a target nucleic acid, which includes: providing an on-chip isotachophoresis (ITP) device, which has a first reservoir containing a leading electrolyte (LE), a second reservoir containing a trailing electrolyte (TE), and a microfluidic channel connecting the first and second reservoirs, wherein a region of the microfluidic channel is provided with a sieving matrix for separating double-strand and single-strand nucleic acids, wherein the first or second reservoirs further containing a spacer ion having a mobility between that of the LE and the TE; providing a probe which is a double-strand nucleic acid formed of a protector strand nucleic acid modified with a fluorescent molecule and a complement strand nucleic acid, wherein the protector strand nucleic acid is released in the presence of the target nucleic acid; adding the probe and a sample to the first reservoir; applying a voltage between the first and second reservoirs; and detecting a fluorescent signal in the microfluidic channel at an interface between the LE and the spacer ion.

In another aspect, the invention provides a method for detecting a target nucleic acid, which includes: providing an on-chip isotachophoresis (ITP) device, which has a first reservoir containing a leading electrolyte (LE), a second reservoir containing a trailing electrolyte (TE), and a microfluidic channel connecting the first and second reservoirs, wherein a region of the microfluidic channel is provided with a sieving matrix for separating double-strand and single-strand nucleic acids, wherein the first or second reservoirs further containing a spacer ion having a mobility between that of the LE and the TE; providing a probe which is a double-strand nucleic acid formed of a protector strand nucleic acid modified with an enzyme and a complement strand nucleic acid, wherein the protector strand nucleic acid is released in the presence of the target nucleic acid; adding the probe and a sample to the first reservoir; applying a voltage between the first and second reservoirs; adding a single strand nucleic acid modified with a substrate of the enzyme to the second reservoir or another reservoir located more downstream than the sieving matrix, the substrate being one that is capable of being converted by the enzyme into a luminescent and/or chromogenic form; and detecting a luminescent and/or chromogenic signal in the microfluidic channel at an interface between the LE and the spacer ion.

It is to be understood that both the foregoing general description and the following detailed description are exemplary and explanatory and are intended to provide further explanation of the invention as claimed.

BRIEF DESCRIPTION OF THE DRAWINGS

FIG. 4 schematically illustrates method according to the first embodiment of the present invention FIG. 5 schematically illustrate an enzyme reaction which can produce luminescent and/or chromogenic signal from their substrates.

FIG. 7 schematically illustrates method according to the first embodiment of the present invention

DETAILED DESCRIPTION OF PREFERRED EMBODIMENTS

Figure 1:
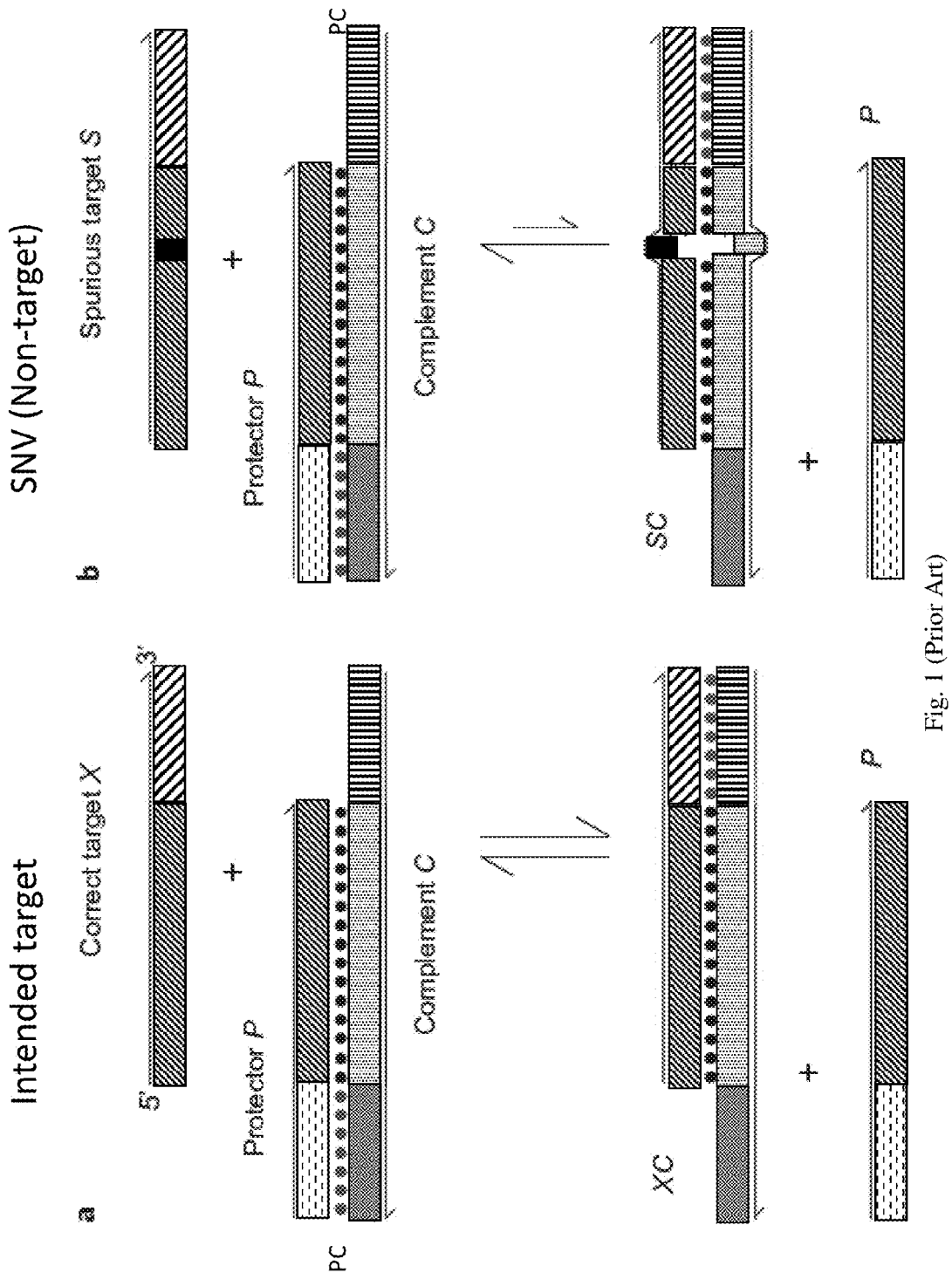
FIG. 1 schematically illustrates a toehold exchange probe useful in high-specificity NA detection.
Figure 2:
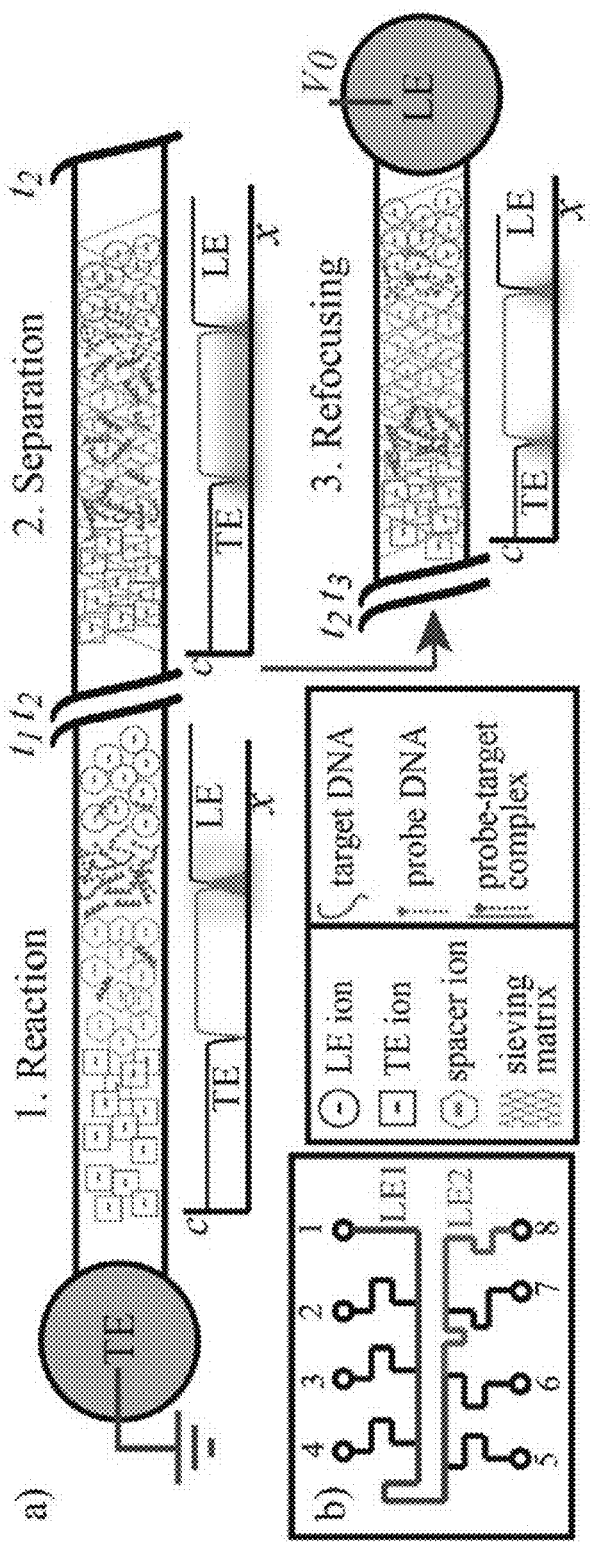
FIG. 2 schematically illustrates an ITP method using an ionic spacer and two-stage separation for high sensitivity DNA hybridization assay.
Figure 3A:
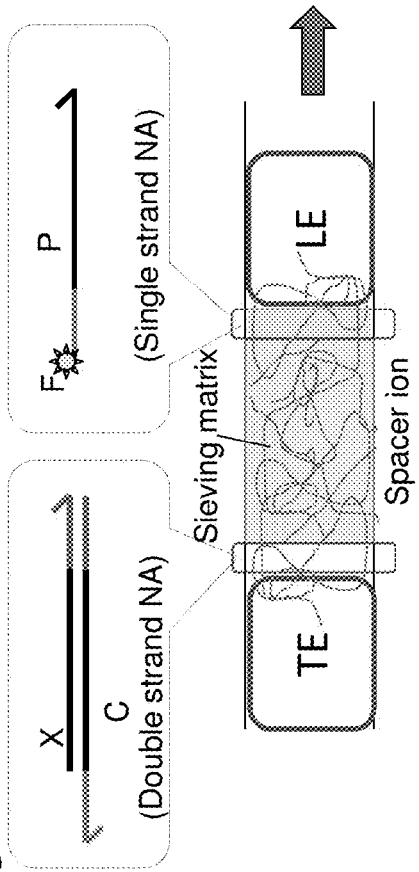
FIGS. 3a-3d schematically illustrate a NA detection method according to a first embodiment of the present invention which uses an ultra-specific DNA probe and on-chip ITP.
Figure 3C:
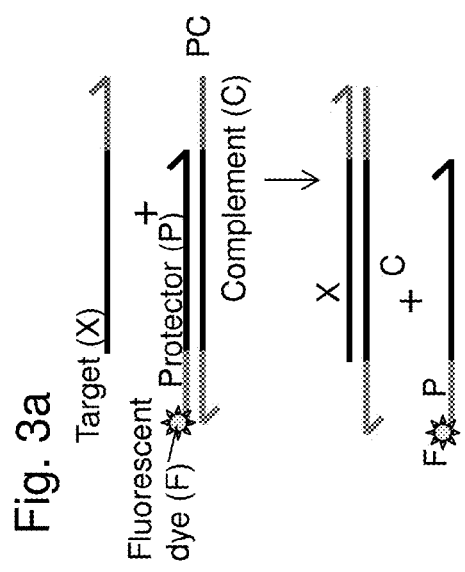
Figure 3B:
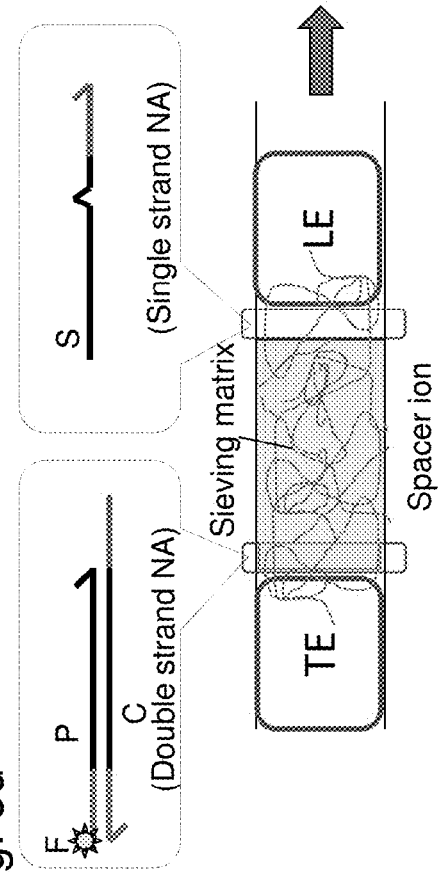

FIGS. 3a-3d schematically illustrates a NA detection method according to a first embodiment of the present invention which uses an ultra-specific DNA probe and on-chip ITP. FIG. 3a illustrates the probe PC and target X and the replacement reaction. The probe PC is similar to that described in Zhang et al. 2012, except that the protector strand P is now modified with a fluorescent dye F. In the presence of the target X, free protector strand P which is fluorescent is generated. As shown in FIG. 3b, by conducting this ultra-specific probe reaction in an on-chip ITP setup similar to that shown in FIG. 2 and described in Eid et al. 2013, where a spacer ion is provided in the sample solution and a sieving matrix is provided in the microfluidic channel, the isolated protector strand P is separated downstream (focused between the spacer ion and leading electrolyte (LE)), and its fluorescent signal is detected there. Also as shown in FIG. 3b, the hybridized NA of target X and complement strand C is focused in the upstream region between the spacer ion and trailing electrolyte (TE).

Figure 3D:
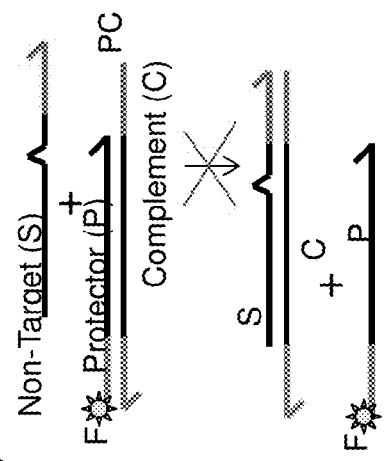

As shown in FIG. 3c, in the absence of the target X or in the presence of a non-target S, free protector strand P is not generated (FIG. 3c); therefore, in the on-chip ITP assay, no fluorescent signal is detected downstream between the spacer ion and LE (FIG. 3d). Rather, fluorescent signal will be present in the upstream region between TE and the spacer ion.

As shown in FIG. 4, a method according to the first embodiment of the present invention includes the following steps: First, an on-chip ITP device is provided, which includes a TE reservoir, an LE reservoir, and a microfluidic channel connecting the TE and LE reservoirs, where a sieving matrix is provided in a region of the microfluidic channel (step S11). Another region of the microfluidic channel between the sieving matrix and the TE reservoir is free of the sieving matrix. The on-chip ITP device may further contain other reservoirs which are connected to the microfluidic channel at various points. Then, the detector double strand PC and a sample (either containing the target X, or containing no target X, or containing a non-target S) are added to the TE reservoir. The spacer ion is added to either the TE or the LE reservoir (step S12). A voltage is then applied between the TE and LE reservoirs (step S13). Fluorescent signals are detected at predetermined regions of the microfluidic channel (between the spacer ion and the LE) (step S14).

Using this technology, 220 fM LOD (limit of detection) within 10 min can be realized.

Figure 5:
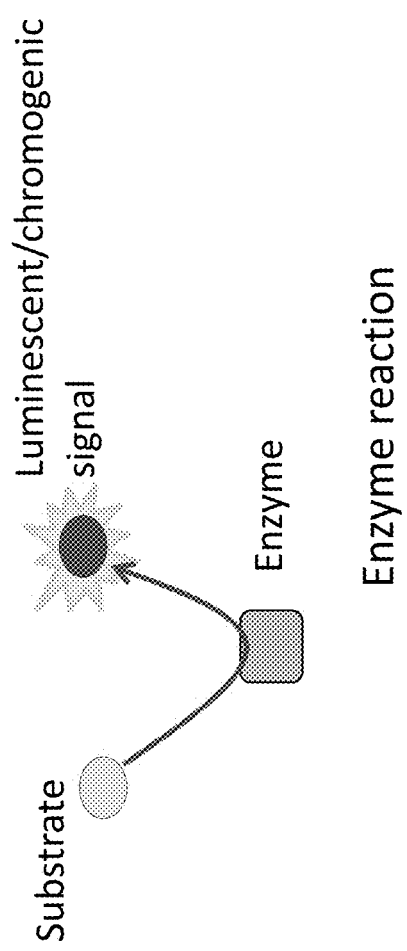
Figure 6:
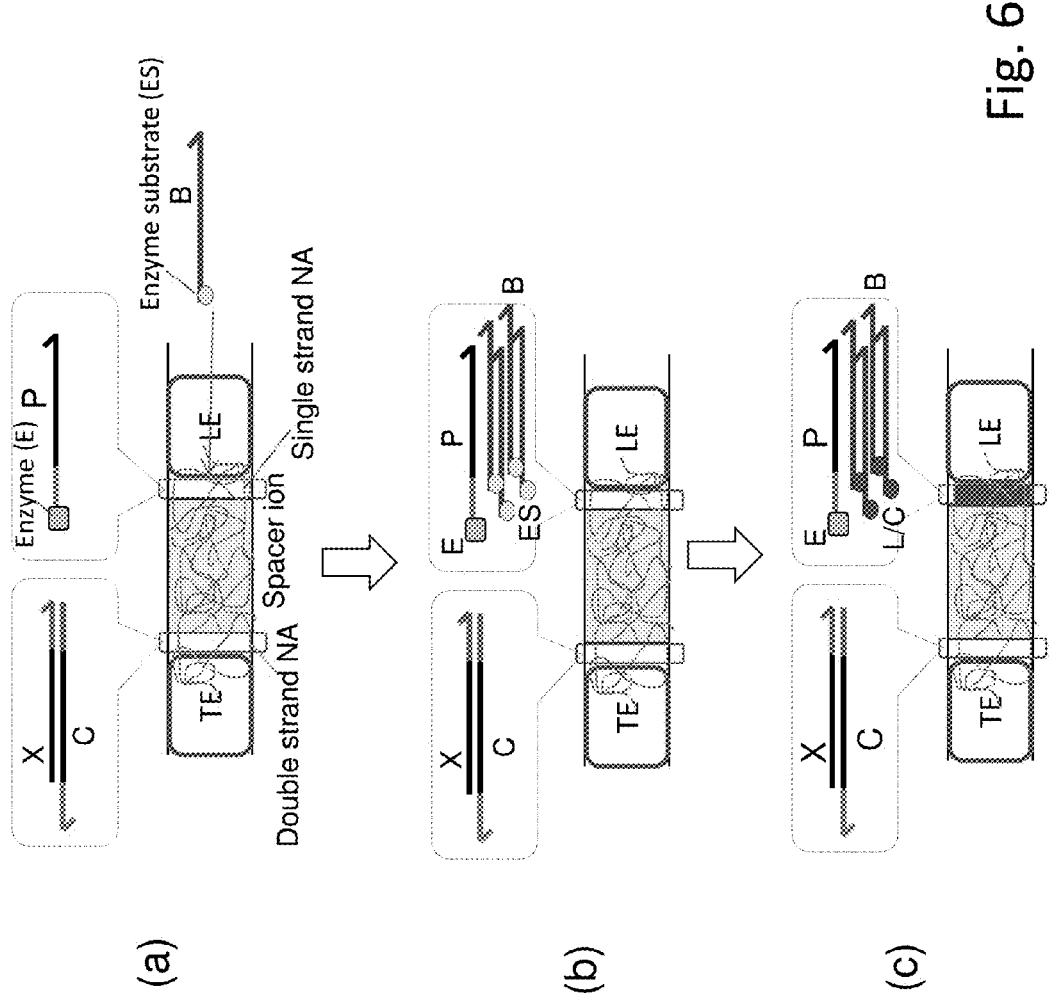
FIG. 6 schematically illustrates a NA detection method according to a second embodiment of the present invention which uses ultra-specific DNA probe with enzyme amplification and on-chip ITP.

FIGS. 5 and 6 illustrate a second embodiment of the present invention which can further improve the detection sensitivity. FIG. 5 schematically illustrate an enzyme reaction which can produce luminescent and/or chromogenic signal from a substrate. If there is sufficient amount of the substrate, the intensity of the luminescent and/or chromogenic signal is proportional to the amount of the enzyme. Since this enzymatic reaction happens multiple times per enzyme, it can be used to improve sensitivity of the ultra-specific probe in the ITP assay.

FIG. 6 schematically illustrates a NA detection method according to the second embodiment, which uses ultra-specific probe with enzyme amplification and on-chip ITP. The on-chip ITP device is similar to that used in the first embodiment. The probe PC in this embodiment (not shown in FIG. 6) is similar to the probe PC in the first embodiment shown in FIG. 3a, except that the protector strand P is now modified with an enzyme E which can catalyze the enzyme reaction shown in FIG. 5, rather than a fluorescent dye. In the presence of the target X, free protector strand P is generated and accumulated in the downstream region between the spacer ion and LE.

Meanwhile, a single strand NA B modified with an enzyme substrate ES, which has the same mobility as the enzyme modified single strand P, is added to the reaction mixture. The substrate-modified single strand B is added to the on-chip ITP device from a position which is more downstream than the position of the spacer ion, preferably at a position after a sufficient length of the sieving matrix (see panel (a)), to avoid reaction of the substrate ES by the enzyme E attached to the double strand probe PC. Since the substrate ES is attached to the single strand B, the substrate is also accumulated in the downstream region (between the spacer ion and LE) along with the free protector strand P (see panel (b)). As a result, enzyme reaction occurs to convert the substrate ES into its luminescent or chromogenic form, and a signal (fluorescent or chromogenic) is generated in the downstream region between the spacer ion and LE (panel (c)). In panel (c), the luminescent or chromogenic form of the substrate is denoted "L/C".

More specifically, for sample injection, the sample including the target X and probe PC is added at the upstream (TE side) of the ITP chip, and the substrate-modified single strand B is added at a downstream position more downstream than the spacer ion, for example, downstream of the sieving matrix, either at the same time the sample is added or later. For example, the substrate-modified single strand B may be added to the LE reservoir of the ITP chip. The spacer ion may also be added to the LE reservoir. The TE, spacer ion and LE will separate under the voltage and the substrate-modified single strand B will move upstream from LE reservoir to the LE-spacer interface.

The method steps according to the second embodiment is summarized FIG. 7, where steps S21, S22, S23 and S24 are similar to steps S11, S12, S13 and S14 of the first embodiment shown in FIG. 4; step S22A is the step of adding the substrate-modified single strand B.

A mixing mechanism may be introduced in the ITP chip to facilitate the enzyme reaction.

In this embodiment, horseradish peroxidase (HRP) or Alkaline Phosphatase (AP) may be used as the enzyme. As the substrate, chemiluminescent substrate (Luminol etc.), chemifluorescent substrate (QuantaBlu, QuantaRed), chromogenic substrate (TMB, DAB, ABTS, OPD, etc.) may be used as the substrate for HRP. Chromogenic substrate (PNPP, BCIP-NBT, etc.) may used as the substrate for AP. Single strand DNA B can be modified with at least one of the above substrates. The single strand S may be modified with multiple substrates, and the substrate may be added anywhere on the single strand B, so long as the modified strand B has approximately the same mobility as the enzyme-modified protector strand P.

Highly-sensitive detection with high-specificity and rapid speed is realized with the second embodiment.

In the first and second embodiments, the fluorescent dye (first embodiment) and the enzyme (second embodiment) may be located anywhere on the protector strand P, so long as they do not interfere with the binding of the protector strand P to the complement strand C. Typically, the fluorescent dye or the enzyme is located at an end of the protector strand P (as shown in FIGS. 3 and 6).

It will be apparent to those skilled in the art that various modification and variations can be made in the NA detection method and related apparatus of the present invention without departing from the spirit or scope of the invention. Thus, it is intended that the present invention cover modifications and variations that come within the scope of the appended claims and their equivalents.

What is claimed is:

1. A method for detecting a target nucleic acid, comprising:
    providing an on-chip isotachophoresis (ITP) device, which has a first reservoir containing a leading electrolyte (LE), a second reservoir containing a trailing electrolyte (TE), and a microfluidic channel connecting the first and second reservoirs, wherein a region of the microfluidic channel is provided with a sieving matrix for separating double-strand and single-strand nucleic acids, wherein the first or second reservoirs further containing a spacer ion having a mobility between that of the LE and the TE;
    providing a probe which is a double-strand nucleic acid formed of a protector strand nucleic acid modified with an enzyme and a complement strand nucleic acid, wherein the protector strand nucleic acid is released in the presence of the target nucleic acid;
    adding the probe and a sample to the first reservoir;
    applying a voltage between the first and second reservoirs;
    adding a single strand nucleic acid modified with a substrate of the enzyme to the second reservoir or another reservoir located more downstream than the sieving matrix, the substrate being one that is capable of being converted by the enzyme into a luminescent and/or chromogenic form; and
    detecting a luminescent and/or chromogenic signal in the microfluidic channel at an interface between the LE and the spacer ion.

2. The method of claim 1, wherein the enzyme is horseradish peroxidase, and the substrate is a chemiluminescent substrate, a chemifluorescent substrate, or a chromogenic substrate.

3. The method of claim 1, wherein the enzyme is alkaline phosphatase, and the substrate is a chromogenic substrate.

* * * * *